United States Patent [19]

Baker et al.

[11] 4,117,166
[45] Sep. 26, 1978

[54] N-(1,1-DIMETHYL-2-PROPYNYL)-ALPHA-(SUBSTITUTED PHENOXY) ALKYLAMIDES AND THEIR USE AS MITICIDES

[75] Inventors: Don R. Baker, Orinda; Francis H. Walker, Mill Valley, both of Calif.

[73] Assignee: Stauffer Chemical Company, Westport, Conn.

[21] Appl. No.: 850,999

[22] Filed: Nov. 14, 1977

Related U.S. Application Data

[63] Continuation of Ser. No. 705,505, Jul. 15, 1976, abandoned, which is a continuation of Ser. No. 591,726, Jun. 30, 1975, abandoned.

[51] Int. Cl.² .................... A01N 9/24; C07C 103/75
[52] U.S. Cl. .............................. 424/324; 260/559 B
[58] Field of Search .................. 424/324; 260/559 R, 260/559 B

[56] References Cited

U.S. PATENT DOCUMENTS

3,272,844  9/1966  Easton et al. .................... 260/559 B

*Primary Examiner*—V. D. Turner
*Attorney, Agent, or Firm*—M. Henry Heines

[57] ABSTRACT

Miticidally active compounds defined by the generic formula

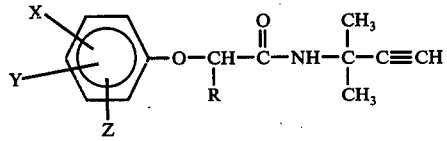

wherein R is either methyl or ethyl, X is either chlorine or fluorine, and Y and Z are either methyl or hydrogen, are described herein.

14 Claims, No Drawings

1

N-(1,1-DIMETHYL-2-PROPYNYL)-ALPHA-(SUBSTITUTED PHENOXY) ALKYLAMIDES AND THEIR USE AS MITICIDES

This is a continuation of application Ser. No. 705,505, filed July 15, 1976, now abandoned which in turn is a continuation of Ser. No. 591,726 filed June 30, 1975, now abandoned.

BACKGROUND OF THE INVENTION

Various substituted amides, particularly N-substituted amides and substituted phenoxy amides, are known to be useful as insecticides, miticides, and herbicides. Typical insecticidal properties of such compounds are taught in U.S. Pat. No. 2,426,885 and its two continuations-in-part, U.S. Pat. No. 2,484,295 and U.S. Pat. No. 2,484,296. Herbicidal properties of such compounds are taught in U.S. Pat. Nos. 3,272,844, 3,439,018 and 3,564,607, and Belgian Pat. No. 739,714.

BRIEF DESCRIPTION OF THE INVENTION

This invention relates to a novel class of substituted acetylenic amides and to their use as miticides when used in a miticidally effective amount. More specifically, this invention relates to N-(1,1-dimethyl-2-propynyl)-α-(substituted phenoxy) alkylamides having the formula

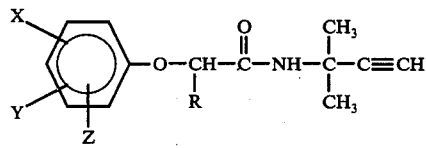

wherein R is either methyl or ethyl; X is either chlorine or fluorine; Y is either 2-methyl or 3-methyl; and where Y is 2-methyl, Z is either hydrogen or 5-methyl; and where Y is 3-methyl, Z is 5-methyl.

By "miticidally effective amount" is meant the amount of the herein disclosed miticidal compounds which when applied to the habitat of mites in any conventional manner will kill or substantially injure a significant portion of the population thereon.

DETAILED DESCRIPTION OF THE INVENTION

The compounds of the present invention can be manufactured by reacting the properly selected phenol with the properly selected N-dimethylpropynyl-2-bromoalkylamide:

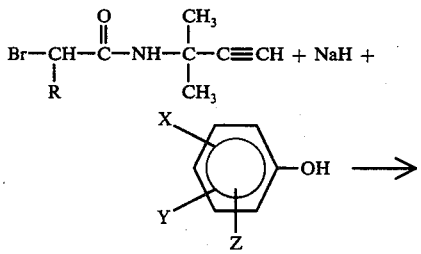

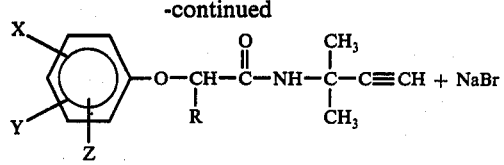

The above-mentioned bromoalkylamide is analogous to compounds known in the art and can be prepared by the method described in Example I below. The amide is added to a mixture of the phenol and sodium hydride in a suitable solvent. After the reaction, the mixture is filtered and the product phenoxyalkylamide is recovered from the filtrate.

In an alternative method, the bromoalkylamide is reacted with the phenol in the presence of potassium t-butoxide:

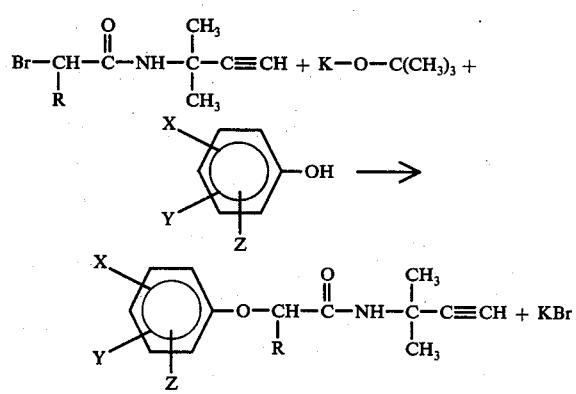

At the completion of the reaction, the product is extracted, washed and recovered.

The examples shown herein are illustrative of the method of preparation of the compounds of the invention.

EXAMPLE I

N-dimethylpropynyl-α-(4-chloro-3,5-dimethylphenoxy) butyramide. (Compound No. 1 in Table I below)

25.0 g (0.12 mole) of 2-bromobutyryl chloride in 25 ml methylene chloride was added dropwise to a mixture of 12.5 g (0.15 mole) of dimethylpropargyl amine and 15.2 g (0.15 mole) of triethylamine in 175 ml methylene chloride with stirring. The mixture was maintained at a temperature of 5° to 10° C. by a cold water bath. The cold bath was removed after the acid chloride addition was complete. After allowing the solution to stand for a half hour, the mixture was washed with 100 ml water, followed by two 100 ml portions of dilute sulfuric acid and two 100 ml portions of sodium bicarbonate solution. Removal of the solvent in a vacuum left 23.5 g (79% yield) of a solid which was N-dimethylpropynyl-2-bromobutyramide, identified by a melting point of 80°–84° C.

1.0 g (0.04 mole) of sodium hydride was suspended in 25 ml of anhydrous tetrahydrofuran in a 300 ml flask which was fitted with a thermometer, a reflux condenser with drying tube, an argon inlet and a stirrer. While the reaction vessel was swept with argon, 6.3 g (0.04 mole) of 4-chloro-3,5-dimethylphenol in 25 ml tetrahydrofuran was added dropwise to the suspension. At the completion of the phenol addition, the mixture was allowed to stand for a half hour. 9.9 g (0.04 mole) of N-dimethyl-propynyl-2-bromobutyramide in 50 ml tetrahydrofuran was then added to the mixture in several portions. The mixture was heated at reflux for 1 hour, cooled and filtered through a pad of Celite®. The filtrate was evaporated and the residue was dissolved in 100 ml methylene chloride. The solution was washed first with water, then with two 100 ml portions of dilute HCL, and finally with two 100 ml portions of 5% $Na_2CO_3$ solution. The solution was dried over $MgSO_4$ and evaporated to give 10.8 g (88% crude yield) of a solid which was recrystallized from hexane to give 6.0 g of a solid identified by infrared spectroscopy to be N-dimethylpropynyl-α-(4-chloro-3,5-dimethylphenoxy) butyramide, m.p. 101°–107° C.

EXAMPLE II

N-dimethylpropynyl-α-(4-chloro-2,5-dimethylphenoxy) butyramide. (Compound No. 2 in Table I below)

6.3 g (0.04 mole) of 4-chloro-2,5-dimethylphenol was added to a solution of 4.7 g (0.04 mole) of potassium tert-butoxide in 80 ml tert-butyl alcohol in a 300 ml flask. 9.9 g (0.04 mole) of N-dimethylpropynyl-2-bromobutyramide, prepared according to the procedure of Example I, dissolved in 20 ml tert-butanol was added to the contents of the flask. The resultant mixture was refluxed for 3½ hours, then cooled and poured into 300 ml water. The resultant mixture was extracted with two 50 ml portions of methylene chloride. The extracts were combined and washed first with two 100 ml portions of dilute HCL, then with two 100 ml portions of 5% $Na_2CO_3$ solution and finally one 100 ml portion of saturated NaCl solution. The extracts were dried over $MgSO_4$ and evaporated to leave 12.0 g (104.8% crude yield) of a solid, which was recrystallized from hexane to give 4.8 g (39.8% yield). The compound was identified by infrared spectroscopy as N-dimethylpropynyl-α-(4-chloro-2,5-dimethylphenoxy) butyramide, m.p. 91°–95° C.

Other compounds, such as those included in the following table, can be prepared in a manner analogous to that shown in the examples above, starting with the appropriate materials. The compounds in the table are representative of those embodied in the present invention. Compound numbers have been assigned to them for purposes of identification throughout the balance of the specification.

TABLE I

| COMPOUND NUMBER | COMPOUND |
|---|---|
| 1 | 4-Cl, 2,6-(CH₃)₂-C₆H₂-O-CH(C₂H₅)-C(O)-NH-C(CH₃)₂-C≡CH |
| 2 | 4-Cl, 2,5-(CH₃)₂-C₆H₂-O-CH(C₂H₅)-C(O)-NH-C(CH₃)₂-C≡CH |
| 3 | 2-Cl, 3,5-(CH₃)₂-C₆H₂-O-CH(C₂H₅)-C(O)-NH-C(CH₃)₂-C≡CH |
| 4 | 4-F, 2,6-(CH₃)₂-C₆H₂-O-CH(C₂H₅)-C(O)-NH-C(CH₃)₂-C≡CH |
| 5 | 4-F, 2,5-(CH₃)₂-C₆H₂-O-CH(C₂H₅)-C(O)-NH-C(CH₃)₂-C≡CH |
| 6 | 4-Cl, 2,5-(CH₃)₂-C₆H₂-O-CH(C₂H₅)-C(O)-NH-C(CH₃)₂-C≡CH |

Miticidal activity on the two-spotted mite [Tetranychus urticae (Koch)] was evaluated as follows:

Pinto bean plants (Phaseolus sp.), approximately 10 cm tall, are transplanted into sandy loam soil in 3-inch clay pots and thoroughly infested with two-spotted mites of mixed ages and sexes. Twenty-four hours later the infested plants are inverted and dipped for 2–3 seconds in 50—50 acetone-water solutions of the test chemicals. Treated plants are held in the greenhouse, and 7 days later mortality is determined for both the adult mites and the nymphs hatching from eggs which were on the plants at the time of treatment. Test concentrations range from 0.05% down to that at which 50% mortality occurs.

The results of the above test procedure on selected compounds from Table I, which indicate the effective concentration at which 50% mortality was achieved, are listed in Table II.

TABLE II

| Effective Concentrations of Two-Spotted Mite [Tetranychus urticae (Koch)] | | |
|---|---|---|
| COMPOUND NUMBER | POST-EMERGENT (%) | EGGS (%) |
| 1 | .01 | .01 |
| 2 | .01 | .03 |
| 3 | .01 | >.05 |

Neither the examples nor the tables above are intended to limit the invention.

The compounds of this invention are generally embodied in a form suitable for convenient application. For example, the compounds can be embodied in miticidal compositions in the form of emulsions, suspensions, solutions, dusts, and aerosol sprays. In addition to the active compounds, such compositions generally contain the adjuvants which are normally found in miticide preparations. One such composition can contain either a single miticidally active compound or a combination of miticidally active compounds. The miticide compositions of this invention can contain as adjuvants organic solvents such as sesame oil, xylene, or heavy petroleum; water; emulsifying agents; surface active agents; talc; pyrophyllite; diatomite; gypsum; clays; or propellants such as dichlorodifluoromethane; or a combination of these. If desired, however, the active compounds can be applied directly to feedstuffs, seeds, or other such matter upon which the pests feed. When applied in such a manner, it will be advantageous to use a compound which is not volatile. In connection with the activity of the presently disclosed miticidal compounds, it should be fully understood that the compounds need not be active as such. The purposes of this invention will be fully served by a compound which is rendered active by an external influence such as light, or by some physiological action which the compound induces when it is ingested into the body of the pest.

The precise manner in which the miticidal compounds of this invention should be used in any particular instance will be readily apparent to a person skilled in the art. The concentration of the active miticide in a typical composition can vary within rather wide limits. Ordinarily, the miticide will comprise not more than about 15.0% by weight of the composition. The preferred range of concentration of the miticide is about 0.1 to about 1.0% by weight.

We claim:

1. A compound having the formula

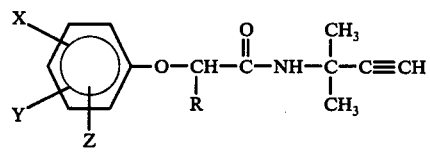

wherein R is either methyl or ethyl; X is either chlorine or fluorine; Y is either 2-methyl or 3-methyl; and where Y is 2-methyl, Z is either hydrogen or 5-methyl; and where Y is 3-methyl, Z is 5-methyl.

2. A compound according to claim 1 in which X is chlorine.

3. A compound according to claim 1 in which R is ethyl.

4. A compound according to claim 1 in which X is chlorine and R is ethyl.

5. A compound according to claim 4 in which X is 4-chloro, Y is 3-methyl, and Z is 5-methyl.

6. A compound according to claim 4 in which X is 4-chloro, Y is 2-methyl, and Z is 5-methyl.

7. A compound according to claim 4 in which X is 5-chloro, Y is 2-methyl, and Z is hydrogen.

8. A method of controlling mites comprising applying to the habitat thereof a miticidally effective amount of a compound having the formula

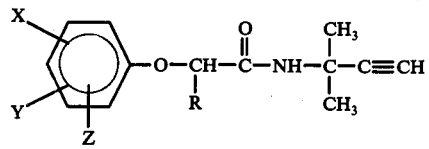

wherein R is either methyl or ethyl; X is either chlorine or fluorine; Y is either 2-methyl or 3-methyl; and where Y is 2-methyl, Z is either hydrogen or 5-methyl; and where Y is 3-methyl, Z is 5-methyl.

9. A method according to claim 8 in which X is chlorine.

10. A method according to claim 8 in which R is ethyl.

11. A method according to claim 8 in which X is chlorine and R is ethyl.

12. A method according to claim 11 in which X is 4-chloro, Y is 3-methyl, and Z is 5-methyl.

13. A method according to claim 11 in which X is 4-chloro, Y is 2-methyl, and Z is 5-methyl.

14. A method according to claim 11 in which X is 5-chloro, Y is 2-methyl, and Z is hydrogen.

* * * * *

UNITED STATES PATENT AND TRADEMARK OFFICE
CERTIFICATE OF CORRECTION

PATENT NO. : 4,117,166
DATED : September 26, 1978
INVENTOR(S) : Don R. Baker et al.

It is certified that error appears in the above-identified patent and that said Letters Patent are hereby corrected as shown below:

In Table I, Column 4, Compound No. 6 should read:

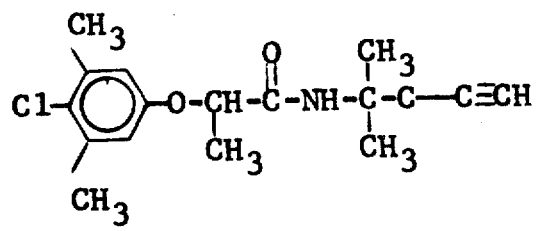

Signed and Sealed this

Ninth Day of October 1979

[SEAL]

Attest:

RUTH C. MASON
Attesting Officer

LUTRELLE F. PARKER
Acting Commissioner of Patents and Trademarks